United States Patent
Dunayevskiy et al.

(10) Patent No.: US 7,179,592 B2
(45) Date of Patent: Feb. 20, 2007

(54) SIZE-EXCLUSION-BASED EXTRACTION OF AFFINITY LIGANDS AND ACTIVE COMPOUNDS FROM NATURAL SAMPLES

(75) Inventors: Yuriy M. Dunayevskiy, Natick, MA (US); Dallas E. Hughes, Milford, MA (US); Andrew S. Weiskopf, Needham, MA (US)

(73) Assignee: Cetek Corporation, Marlborough, MA (US)

( * ) Notice: Subject to any disclaimer, the term of this patent is extended or adjusted under 35 U.S.C. 154(b) by 64 days.

(21) Appl. No.: 09/920,435

(22) Filed: Aug. 1, 2001

(65) Prior Publication Data

US 2002/0052006 A1 May 2, 2002

Related U.S. Application Data

(63) Continuation-in-part of application No. PCT/US00/03562, filed on Feb. 11, 2000.
(60) Provisional application No. 60/119,966, filed on Feb. 12, 1999.

(51) Int. Cl.
*C12Q 1/68* (2006.01)

(52) U.S. Cl. .................. 435/6; 210/198.2; 210/635; 210/650; 210/656; 530/414; 530/417; 435/7.1; 435/7.93

(58) Field of Classification Search .......... 435/4, 435/6, 7.1, 7.2, DIG. 2, 173, 501; 210/198.2, 210/635, 650, 656; 530/414, 417; 436/501, 436/173

See application file for complete search history.

(56) References Cited

U.S. PATENT DOCUMENTS

| | | | |
|---|---|---|---|
| 5,783,397 A | 7/1998 | Hughes et al. | 435/7.1 |
| 5,891,742 A | 4/1999 | Dollinger et al. | 436/538 |
| 5,948,231 A | 9/1999 | Fuchs et al. | 204/601 |
| 6,207,861 B1 * | 3/2001 | Nash et al. | 564/133 |

FOREIGN PATENT DOCUMENTS

| WO | WO 97/01755 | * | 1/1997 |
|---|---|---|---|
| WO | WO 01/94943 | | 12/2001 |

OTHER PUBLICATIONS

Van Breemen, R. B.; Huang, C. –R.; Nikolic, D.; Woodbury, C. P.; Zhao, Y. –Z.; Venton, D. L. "Pulsed Ultrafiltration Mass Spectrometry: A New Method for Screening Combinatorial Libraries" Anal. Chem. 1997, 69, 2159–2164.*

Moy et al., "MS/NMR: A Structure–Based Approach for Discovering Protein Ligands and for Drug Design by Coupling Size Exclusion Chromotography, Mass Spectrometry and Nuclear Magnetic Resonance Spectroscopy", Anal. Chem., vol. 73, pp. 571–581, (2001).

Berthonneau et al., "*Taxoplasma gondii*: Purification and Characterization of an Immuogenic Metallopeptidase", Experimental Parasitology, vol. 95, pp. 158–162, (200).

van Breemen et al., "Pulsed Ultrafiltration Mass Spectrometry: A New Method for Screening Combinatorial Libraries", Anal. Chem., vol. 69, pp. 2159–2164, (1997).

Blom, K. F. et al., "Determining Affinity–Selected Ligands and Estimating Binding Affinities by Online Size Exclusion Chromatography/Liquid Chromatography–Mass Spectrometry", J. Comb. Chem. 1(1):82–90 (1999).

Dunayevskiy, Y. M. et al., "Simultaneous Measurement of Nineteen Binding Constants of Peptides to Vancomycin Using Affinity Capillary Electrophoresis–Mass Spectrometry", J. Med. Chem. 41:1201–1204 (Feb. 1998).

Siegel, M. M. et al., "Rapid Methods for Screening Low Molecular Mass Compounds Non–Covalently Bound to Proteins Using Size Exclusion and Mass Spectrometry Applied to Inhibitors of Human Cytomegalovirus Protease", J. Mass Spectro. 33:264–273 (1998).

Dunayevskiy, Y. M. et al., "Mass Spectrometric Identification of Ligands Selected From Combinatorial Libraries Using Gel Filtration", Rapid Commun. Mass. Spectrom. 11:1178–1184 (1997).

Kaur, S. "Affinity Selection and Mass Spectrometry–Based Strategies to Identify Lead Compounds in Combinatorial Libraries", J. Protein Chem. 16(5):505–511 (1997).

Zhao, Y. et al., "Screening Solution–Phase Combinatorial Libraries Using Pulsed Ultrafiltration/Electrospray Mass Spectrometry", J. Med. Chem. 40:4006–4012 (1997).

* cited by examiner

*Primary Examiner*—Jon Epperson
(74) *Attorney, Agent, or Firm*—Weingarten, Schurgin, Gagnebin & Lebovici, LLP

(57) ABSTRACT

The invention encompasses an improved, rapid, size-exclusive method for screening for small molecular weight ligands that bind specifically to a protein target, using size-exclusion separation, ultrafiltration, and mass spectrometry.

22 Claims, 7 Drawing Sheets

SIZE-EXCLUSION-BASED EXTRACTION OF AFFINITY LIGANDS AND ACTIVE COMPOUNDS FROM NATURAL SAMPLES

CROSS REFERENCE TO RELATED APPLICATIONS

This application claims benefit of U.S. Provisional Application 60/119,966, filed Feb. 12, 1999, and International Application No. PCT/US00/03562, filed Feb. 11, 2000, the whole of which are hereby incorporated by reference herein.

BACKGROUND OF THE INVENTION

The present invention relates to screening complex biological materials, such as natural samples, natural products, and combinatorial libraries, for active compounds such as affinity ligands. In particular, active compounds are extracted using size-exclusion separation and ultrafiltration, and are subjected to subsequent analysis. The analysis may include structural or functional characterization of an isolated active compound by any one of many techniques known to one of ordinary skill in the art of screening complex biological materials. Suitable analytical techniques include, but are not limited to, mass spectrometry, liquid and other chromatography, a secondary assay, and the like.

Testing complex biological samples for new drug candidates in high throughput screening programs is a successful strategy employed by the pharmaceutical industry. Once an active sample is identified, however, it can be difficult to isolate the active compound, particularly from natural product extracts or natural samples.

Natural samples such as natural extracts represent a highly and chemically diverse collection of compounds that include very small to very large molecules, which makes it very difficult to isolate any single active compound. An active compound is one that has an effect on a biological molecule such as a protein or nucleic acid. For instance, active compounds include affinity ligands that can bind to the biological molecule. As most successful drug compounds are of small molecular weight (less than 2,000 Daltons), separations based on size can be a useful tool in assisting the isolation of active components from natural samples. The present invention enables high-throughput screening of such complex biological materials for identification of active ligands to a biological target molecule.

Combinatorial chemistry offers the means to generate a large number of different chemicals simultaneously. Modern analytical methods allow the screening of such combinatorial libraries to select those compounds possessing desirable properties. However, these methods have their limitations, so that a need remains, too, for a successful analytical methodology that provides high throughput screening of combinatorial libraries against biological targets for identification of active ligands.

Screening a library generally involves a binding or a functional assay to determine the extent of ligand-receptor interaction. Often, either the ligand or the receptor is immobilized on a solid surface (e.g. polymer bead or plate) and, after detection of the binding or the functional activity, the ligand is released and identified by a different means, for example, by mass spectrometry. Solid-phase screening assays offer faster isolation and identification of active analytes compared to the solution-based methods. On the other hand, limitations associated with heterogeneous assays create a demand for a breakthrough technology for rapid and efficient screening of natural samples screened in solution. Solution-phase assays are desirable to increase screening specificity, but current methodologies involve iterative processes that are long and laborious.

Recently, electrospray ionization mass spectrometry (ESI-MS) has also been used in screening, directly or in conjunction with a solution-based screening method. The direct screening of combinatorial libraries by ESI-MS relies on its ability to characterize non-covalent complexes of proteins bound to ligands (i.e., to distinguish between a protein target and its ligand, even a small one). Alternatively, mass spectrometry can be coupled, on-line or off-line, with solution-based screening methodologies, as a final dimension for structure determination of biologically active compounds.

One method, the Hummel-Dreyer method, recently used for binding studies of small molecules to proteins, is based on size separation of the receptor protein and its ligand by gel filtration. The approach of separating a receptor (i.e., a target protein) and a receptor-ligand complex from other small, unbound molecules on the basis of size differences, was first applied to the separation of antibody-peptide complexes from the rest of a peptide library, with subsequent analysis of the ligands on reversed-phase high-performance liquid chromatography (RP-HPLC) (R. N. Zuckerman et al., Proc. Nat. Acad. Sci., USA 89:4505–4509 (1992), J. M. Kerr et al., Bioorg. Med. Chem. Lett. 3:463=468 (1993)).

Size-exclusion separation has also been applied to small molecule combinatorial libraries. Some work has been done on developing a methodology for selection and identification of ligands with high affinity to a biological target using a size-exclusion-complex isolation procedure and mass spectrometry: e.g., Y. Dunayevskiy et al., Rapid Comm. Mass Spec., 11:1178–84 (1997); M. M. Siegel et al., J. Mass Spec., 33:264–273 (1998). These attempts to screen combinatorial libraries and other complex mixtures of compounds on the basis of size-exclusion separation have had limited success in actual application, particularly under the rigors of high throughput screening. One major problem has been the tendency of transfer lines and other conduits used in high-throughput, size-exclusion-complex isolation screening protocols, particularly transfer lines to reverse phase HPLC column, to become clogged and impassable after only 1–2 hours of operation. Such clogging, which occurs due to irreversible collection of the protein on the stationary phase of the HPLC column, necessitates frequent changes of the transfer lines. It also is a limiting factor in the overall effectiveness and on-line automation of such screening protocols. This effect is even more pronounced when dealing with complex biological mixtures such as natural samples that contain large MW biomolecules. Therefore, a need has remained for a size-exclusion-based screening method that can effectively extract active ligands from natural samples and simultaneously withstand high throughput conditions.

BRIEF SUMMARY OF THE INVENTION

The present method combines affinity interactions with size exclusion methods to enable rapid isolation and characterization of small molecule compounds from highly complex mixtures such as natural samples.

Also, the advantage of the present method's combination of techniques is that it allows one to screen pools of compounds simultaneously, instead of one compound at a time. The present invention provides an improved method of rapidly extracting, from complex biological materials such as natural samples, active compounds like affinity ligands, by using a unique combination of both size-exclusion separation (e.g., by gel filtration) and ultrafiltration steps, for further analysis and characterization. The analysis can take the form of, e.g., mass spectrometry (MS), high-performance liquid chromatography (HPLC) or other chromatography, and/or a secondary assay. One advantage of the present method is that it allows sustained, high-throughput screening, without having to replace HPLC or other analytical columns for at least 7 days, when coupled to HPLC or the like.

In general, the rapid screening method of the invention comprises the following main steps in the order given:

(i) mixing and incubating a protein target (TG) with a natural sample potentially containing a small molecular weight, affinity ligand (L) (in particular, a natural sample), to form a reaction mixture, under conditions conducive to ligand/target (L/TG) complex formation in solution;

(ii) removing from the reaction mixture, unbound, small molecular weight material that is present in the biological sample, by using a size-exclusion medium that, based on molecular weight differences, separates out and retains small molecule compounds while allowing proteins or bound ligand/protein target (L/TG) complexes to pass through;

(iii) subjecting the size-excluded reaction mixture, now containing only large molecular weight materials like unbound proteins and bound L/TG complexes, to conditions conducive to L/TG complex dissociation, to yield free, small molecular weight ligand (L) and target (TG) in solution, and using a second size-exclusion medium, e.g., an ultrafiltration membrane, to isolate the free ligand from the protein target and other large molecules remaining in the size-excluded reaction mixture from step (ii); and (iv) subjecting the isolated ligand to an analytical technique in order to identify it structurally and/or functionally, such as mass spectrometry (MS), or chromatography, an alternative binding assay, or a secondary functional assay.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1:
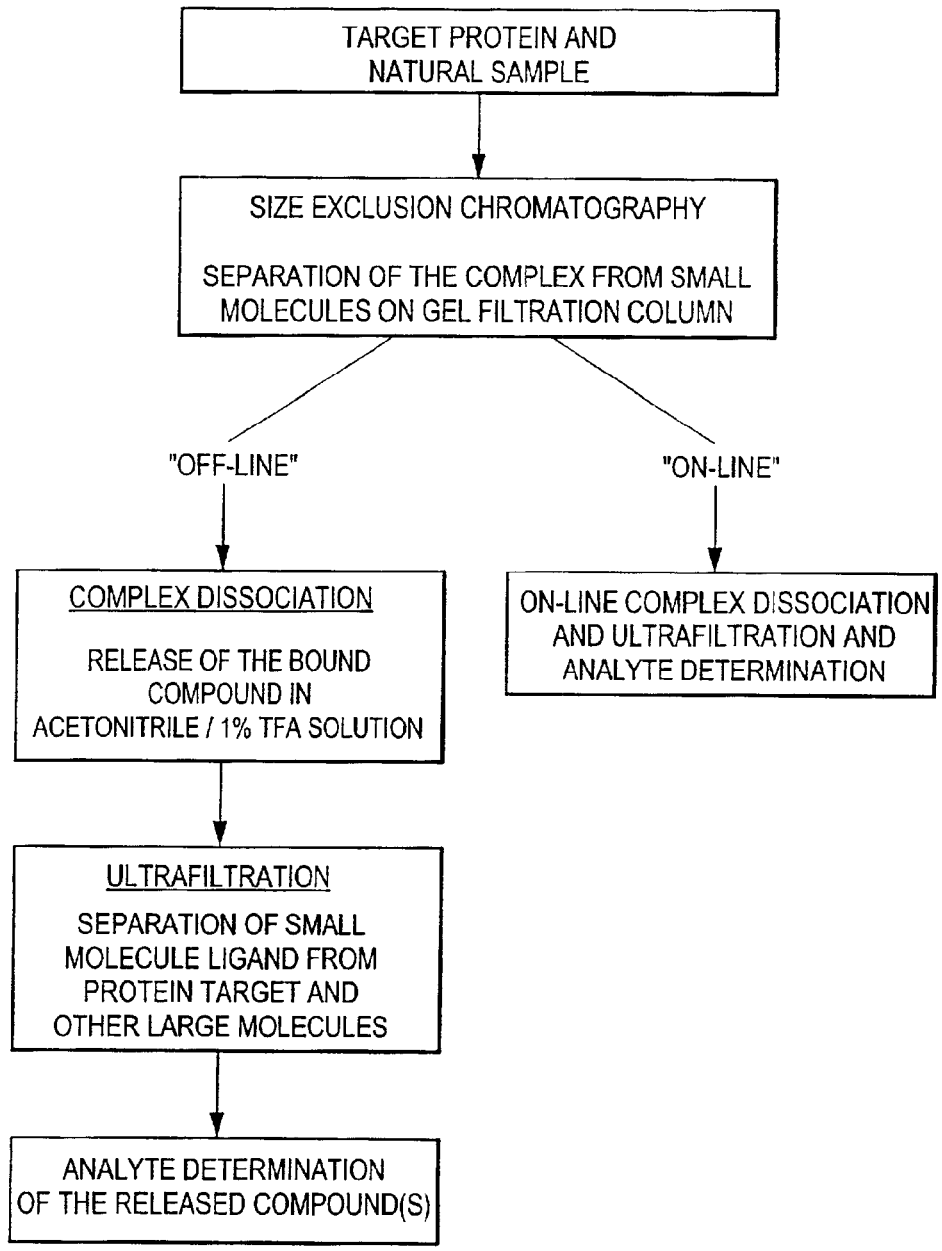
FIG. 1 is a flowchart of the general steps of the method.

The invention provides an improved, high-throughput, size exclusion method of screening complex biological material for active compounds, using size-exclusion separation and ultrafiltration to extract candidate active compounds. Any such isolated compound is subsequently subjected to a known analytical technique for characterizing that compound, including, but no limited to, mass spectrometry, liquid or other chromatography, infrared (IR) spectroscopy, or nuclear magnetic resonance (NMR). In addition, the isolated compound can be tested in a functional secondary assay, including, but not limited to, cellular assays. It allows the screening of several pools of compounds at one time, as well as complex mixtures and natural samples containing molecules of very different MW sizes.

This invention uses a unique combination of steps to extract candidate active compounds from a natural sample: allowing binding of a small molecular weight, affinity ligand (L) to a protein target (TG) in solution; size-exclusion separation of larger molecules, including the ligand/protein (L/TG) complex, from smaller, unbound, target-inactive material; subsequent dissociation of the L/TG complex and isolation of the target-binding ligand (L) through another size-based separation, particularly ultrafiltration, of the small ligand (L) from large molecules (i.e., the target and other proteins). The ligand can then be identified and/or further characterized by known techniques, including but not limited to mass spectrometry (MS) alone or in conjunction with liquid chromatography (LC-MS), NMR, IR spectroscopy, and functional secondary assays such as cellular assays. Examples include but are not limited to an alternative binding assay, a biochemical assay, a cell-based reporter assay, or an ELISA-based assay.

"Small molecules" or "small molecular weight molecules" are understood in the art to refer to compounds with a molecular weight of about 2,000 Daltons or less. Advantageously, the method can detect and isolate from a screened complex biological sample, target-binding ligands of about 2,000 Daltons or less, more preferably 1500 Daltons or less, even 1000 Daltons or less. Examples of small molecular weight ligands that may be identified in natural extracts by the present method include but are not limited to polyketides, terpenes, alkaloids, and quinones.

Large molecular weight compounds are generally those having a molecular weight of about 8,000 Daltons, more typically 10,000 Daltons or higher. Examples include proteins as well as complexes of proteins noncovalently bound to small molecule ligands.

As known by those of ordinary skill in the art, natural samples, extracts, products, or the like, include both small and large molecular weight molecules. It is also appreciated that natural samples include, but are not limited to, extracts of terrestrial and marine plants, cells from higher animals including humans, eubacteria, actinomycetes and other bacteria, microbial fermentation broths, both filamentous and non-filamentous fungi, protozoa, algae, archaebacteria, worms, insects, marine organisms, sponges, corals, crustaceans, viruses, phages, tissues, organs, blood, soil, sea water, fresh water, humus, detritus, manure, mud, and sewage.

The general method of the invention is outlined in the flowchart of FIG. 1.

In one aspect, the invention provides a method of screening a complex biological sample for an affinity ligand that binds to a protein target. The method preferably includes the following steps in the order given:

(1) mixing a protein target and a complex natural sample in solution to form a reaction mixture;

(2) incubating the reaction mixture under conditions allowing complex formation by the target and any target-binding ligand present in the sample;

(3) passing the reaction mixture through a first size-exclusion medium that removes from the reaction mixture any small molecular weight compound having a molecular weight less than a first preset value (e.g., the first preset value may lie in the range of 5000 Daltons or less, with the cut-off being about 3000 Da);

(4) subjecting the size-excluded reaction mixture from step (3) to conditions promoting dissociation of any ligand/target complex into free ligand and free target; and (5) passing the reaction mixture resulting from step (4) through a second size exclusion medium that removes from the reaction mixture any molecule larger than a second preset value.

As desired, after step (5), one performs an additional step: (6) subjecting the reaction mixture resulting from step (5). to at least one analysis or secondary assay. For instance, one of the following analyses could be performed: (a) mass spectrometry analysis, or (b) liquid chromatography coupled on-line with mass spectrometry, or (c) a functional assay, thereby characterizing any small molecular weight ligand remaining in the reaction mixture resulting from step (5). Alternatively or additionally, the doubly size-excluded reaction mixture from step (6) may be subjected to a secondary assay, such as a binding assay or enzymatic assay, a biochemical assay, a cell-based reporter assay, an ELISA-based assay, or other functional assay.

In another aspect, the method of the invention further comprises comparing the analytical results of step (6) with a reference standard. The reference standard preferably comprises the analytical results, (e.g., MS or LC-MS results) of subjecting either a sample of the protein target alone or a mixture of the protein target with a non-target-binding complex biological material sample, to steps (2)–(6) of the method.

The rapid extraction/screening method of the invention can be performed in an on-line or off-line format. Additionally, the method can further include a competitive-binding embodiment, as a control to determine whether a ligand detected by the method binds to the selected protein target specifically (at the same site as a known competitive ligand) or non-specifically (at another site, e.g., by hydrophobic interactions).

Off-line Embodiment

The target protein (TG) is initially incubated with a natural sample, in solution, for a time period sufficient to reach equilibrium or near equilibrium binding of any ligand (L) to the target (e.g., about 5–60 minutes, preferably 5–10 minutes). Then the physical separation of an L/TG complex from unbound small molecule compounds is achieved on a size-exclusion medium, such as a gel filtration column (e.g., Pharmacia HR 10/10 columns), which provides separation of large molecules (e.g., target protein (TG) and other proteins in the sample) and large complexes (i.e., L/TG complex) from unbound, small molecular weight compounds in the natural sample. Non-binding small molecules in the target/sample mixture are retained by the gel-filtration column. Large molecules elute with the void column volume. Therefore, after this separation step, the size-excluded reaction mixture contains unbound TG and L/TG complex, as well as other large molecules initially present in the biological sample, all of which is eluted in the void column volume.

Then a solution, comprising at least one organic solvent and at least one organic acid (e.g., 100 μL acetonitrile (ACN) solution containing 0.1% trifluoroacetic acid (TFA)), is added to the first size-excluded reaction mixture eluted from the gel filtration column. This step creates conditions for protein denaturation and consequent release of bound ligand from target, i.e., dissociation of the bound L/TG complex into unbound or free L and TG. The whole resulting mixture is then loaded onto a second size-separation medium, such as an ultrafiltration membrane having a small molecular weight cut-off, e.g., in the range of about 1,000–5000 Daltons (Da), preferably about 2,000–4,000, most preferably about 3,000 Da. Only molecules smaller than the ultrafiltration membrane's cut-off can pass through. Thus, this second size-separation step provides isolation of the dissociated ligand molecules from all large molecules in the screened biological sample. Small molecules remaining in the mixture after the first size-exclusion step (i.e., an affinity ligand having the desired affinity to the protein target), pass through the ultrafiltration membrane, while the membrane surface retains all large molecules (i.e., target and other large MW molecules originating from the sample).

The remaining, ultrafiltered reaction mixture or material is collected and subjected to an analysis or assay of choice. For instance, it could be subjected to MS alone or by liquid chromatography coupled on-line with MS (LC-MS), to analyze any target-binding ligand isolated by the ultrafiltration step. Alternatively or additionally, the isolated target-binding ligand could be subjected to a secondary, binding or other functional assay.

On-line Embodiment

Figure 2A:
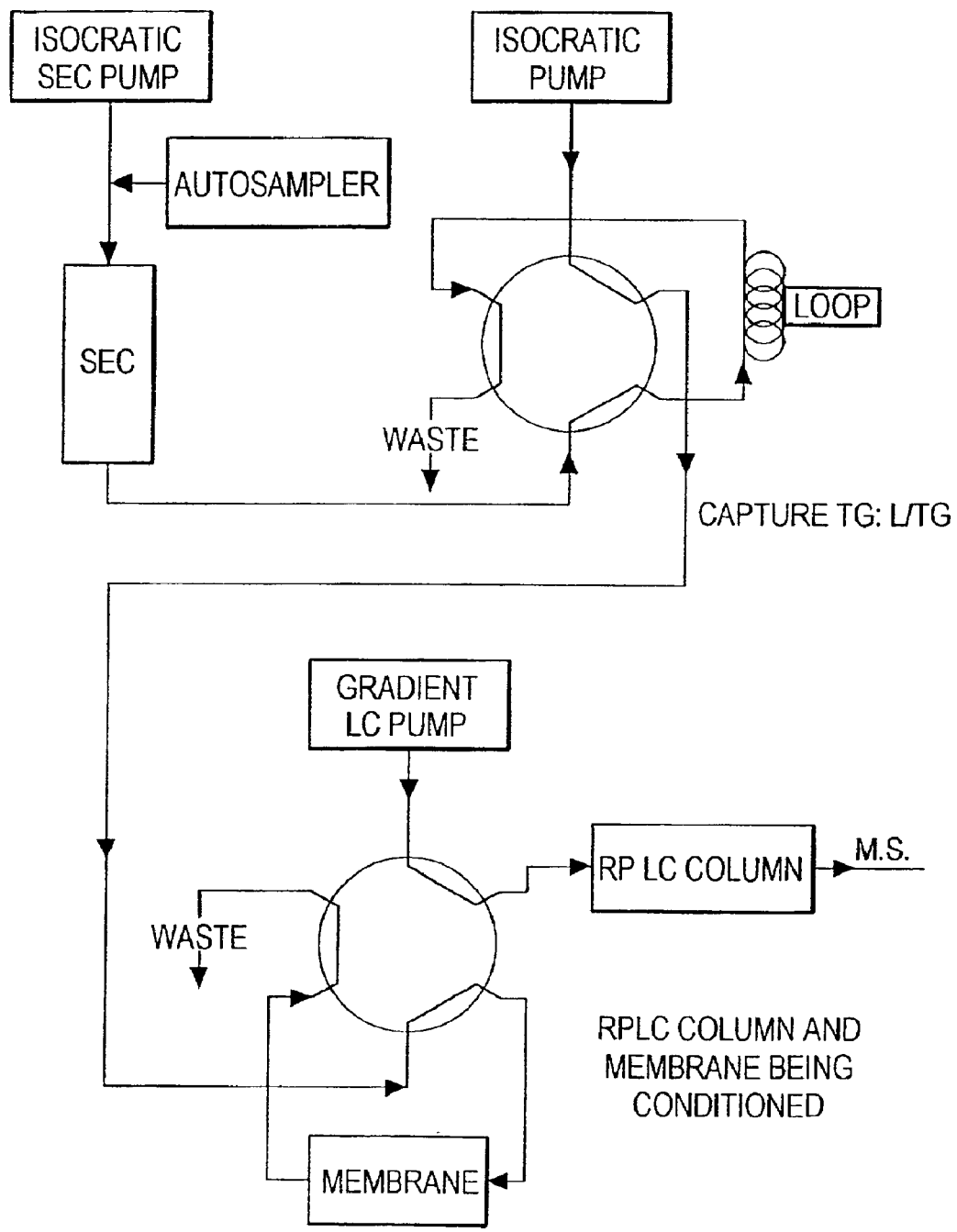
FIGS. 2A, 2B, and 2C show a schematic representation of an apparatus set-up for practicing an on-line embodiment of the screening method of the invention, at different time-points in the method.
Figure 2B:
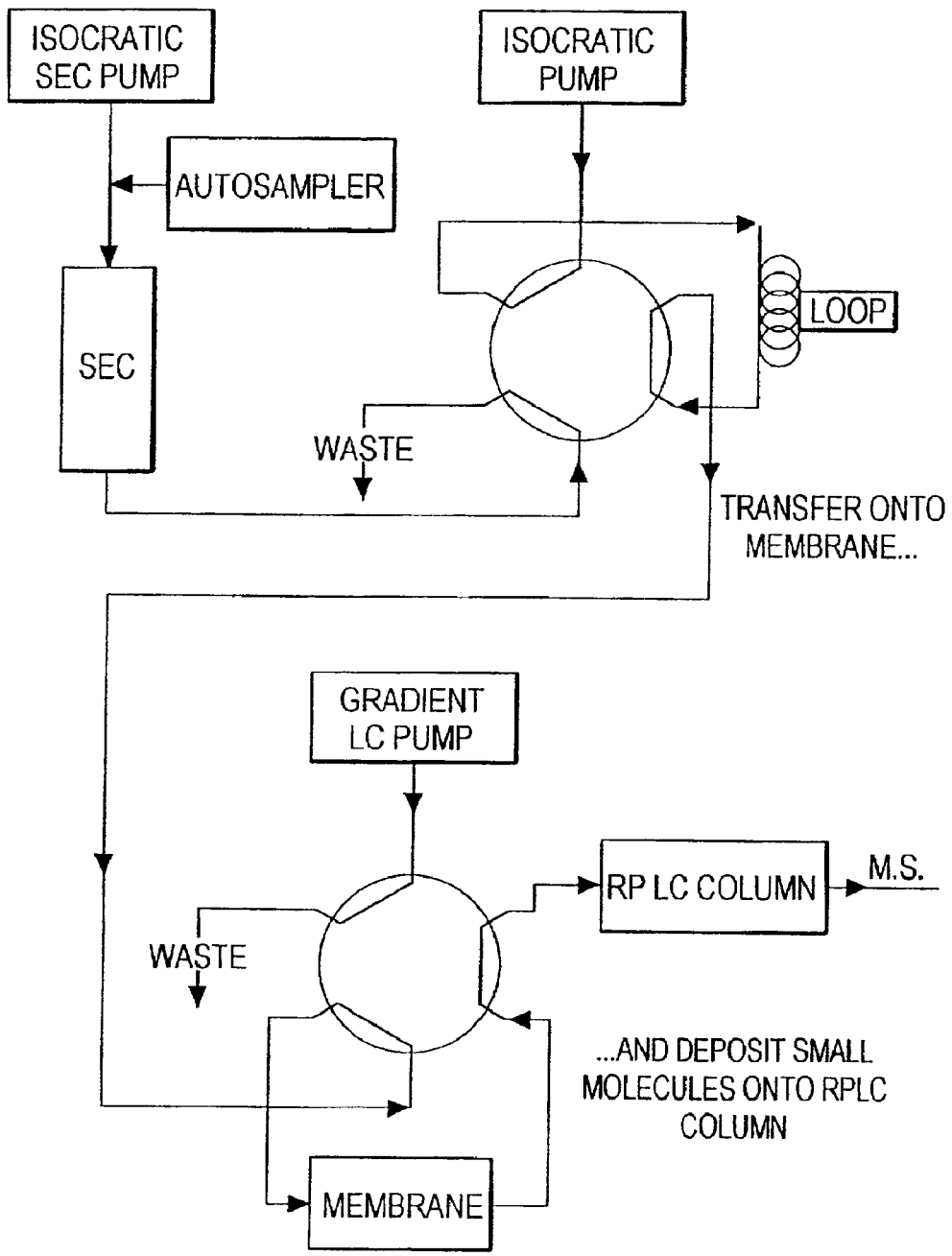
Figure 2C:
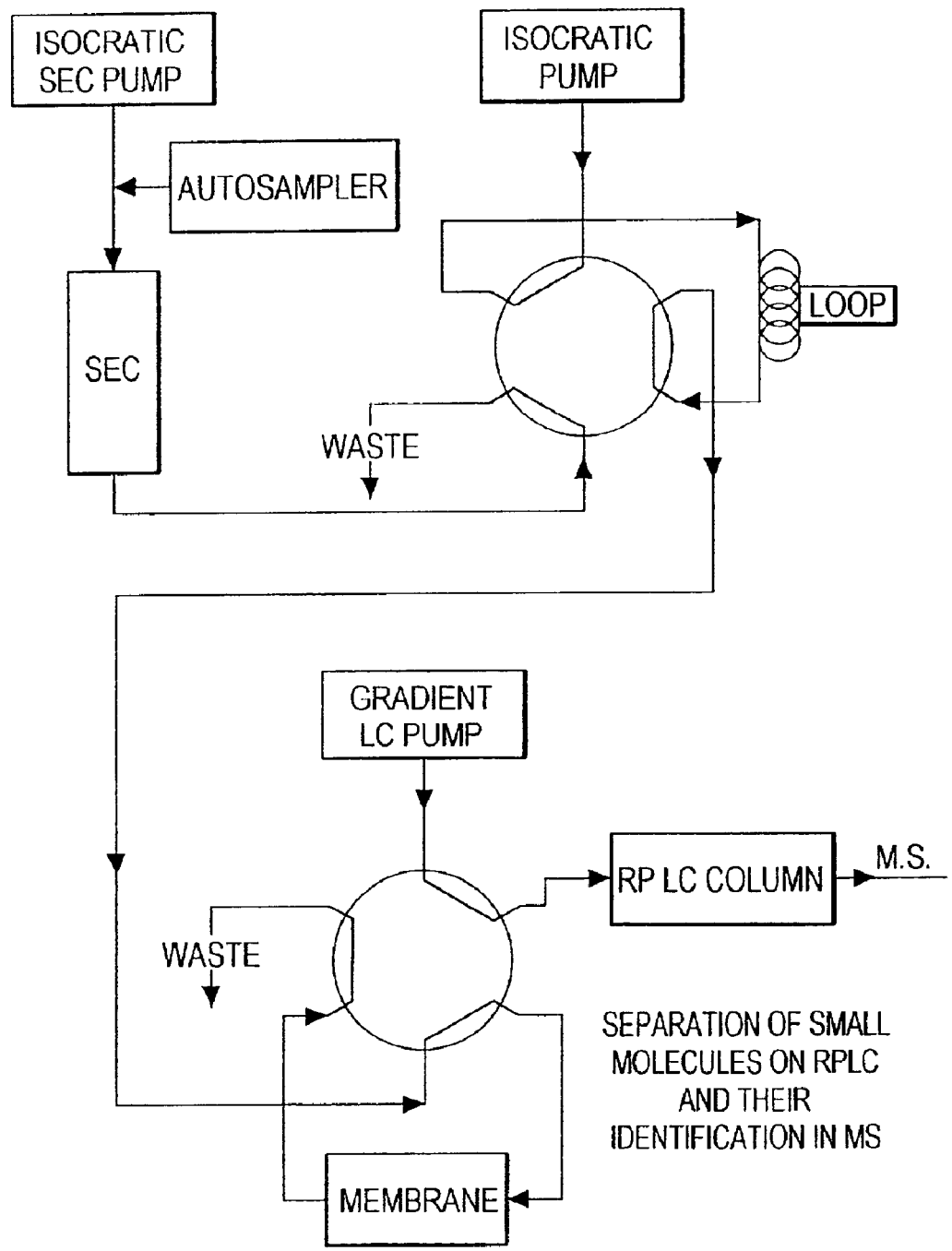

In an on-line format, the size-exclusion column (SEC), the ultrafiltration membrane, and liquid chromatography-mass spectrometry (LC-MS) system are assembled together on-line. One of the possible instrumental arrangements to carry out the method of the invention is shown in FIGS. 2A, 2B, and 2C, which depict the method and instruments at different time points. FIG. 2A shows the isolation and trapping of large molecular weight biomolecules in the loop. FIG. 2B shows the transfer of the isolated large molecular weight biomolecules onto an ultrafiltration membrane, together with application of conditions conducive to ligand/target complex dissociation, the separation of any dissociated ligand from the target, and deposition of the isolated ligand on a reverse-phase LC column. FIG. 2C shows the characterization of the ligand, after ultrafiltration, by LC-MS analysis.

In the on-line method, after incubation of the reaction mixture for a time sufficient to allow target-ligand binding (e.g., within about 5–60 minutes), the mixture is injected into the SEC, and large molecules come out first, non-retained by the SEC stationary phase of the SEC. Small molecules are retained in the pores of the SEC stationary phase. The chromatographic peak corresponding to large molecules is forwarded into a sample loop (FIG. 2a), and the remaining flow from the SEC is then diverted into waste. The solution containing organic solvent (e.g., acetonitrite (ACN)) acid (TFA)) and organic acid (e.g., acetic acid or trifluoroacetic acid (TFA)) is then added to the sample in the loop, in order to provide conditions for L/TG complex dissociation. At the same time, sample is transferred into the chamber of the ultrafiltration membrane (FIG. 2b). Then the sample is pumped through the ultrafiltration membrane directly into an analysis instrument of choice, such as a MS and/or a LC column for further MS, LC, or LC-MS analysis of the released ligand (FIG. 2c). Only the released small molecule ligand is able to pass through the membrane, and is subsequently identified by MS or LC-MS. Alternatively, the sample may be pumped through the ultrafiltration membrane into an assay set-up of choice.

Competitive Binding Embodiment

Another embodiment of the invention combines the use of competitive binding along with the described screening assay. Utilization of a known competitive ligand (CL) that binds to a selected target allows determination of whether the active ligand extracted from a biological mixture is bound to a specific binding site or known site of the target protein. In this case, a CL that binds to a known site is added to the reaction mixture of target and biological sample containing a small molecular weight affinity ligand at the first, mixing and incubation stage. The resulting mixture of target/natural sample/known competitive ligand can be subjected to the two size-exclusion steps of the invention, as previously described. As needed, a dissociation step may be performed as previously discussed, to remove protein prior to analysis of any detected small molecule ligands. During mass spectrometry, MS-LC, or whatever analysis is performed, both ligand (L) and competitive ligand (CL) signals are monitored. If the analyzed signal, e.g., a MS signal, of the extracted ligand L is unaffected by the presence of CL in the binding mixture, one concludes that the identified ligand L binds to a different site from the CL binding site of TG. This competitive-binding approach thus allows one to identify ligands binding to different sites of the target. For example, this could be used to quickly eliminate non-specific binders detected during the screening method, as not being candidate compounds for regulating the activity of the target protein. Instead, one can focus further screening, testing and/or characterization efforts on those ligand molecules (L) whose binding to the target diminishes upon inclusion of the known competitive ligand in the reaction mixture. Such a result suggests that the candidate ligand from the screened sample thus binds to the same site on the protein target as does the known competitive ligand.

In the competitive binding embodiment of the method, the reference standard for determining whether a screened sample contains a specific target-binding ligand, comprises the analytical results of subjecting a mixture of the protein target and the known competitive ligand, in the absence of any other target-binding ligand, to steps (2)–(6). For instance, the results could be the profile of that mixture's MS or LC-MS signals.

The following examples are presented to illustrate the advantages of the present invention and to assist one of ordinary skill in making and using the same. These examples are not intended in any way otherwise to limit the scope of the disclosure.

Exemplary Protocols and Materials
Exemplary Gel Filtration Isolation Protocol

Stock solutions of candidate compounds used for assaying their binding to a protein target (e.g., human carbonic anhydrase II (CAII)), can be prepared by dissolving them in a 1:1 (v/v) mixture of acetonitrile (HPLC Grade; Fisher Scientific, Springfield, N.J., USA) (ACN) and buffer A, and diluting to a concentration of 10 times higher than the desired concentration in the binding assay. The target protein stock solution can be prepared by dissolving and diluting the target in buffer A. Binding mixtures consisted of 50 μL target stock with 5 μL of the candidate compounds stock. The reaction mixtures are incubated at room temperature for 1 hr, after gentle mixing by pipette. The gel filtration columns (e.g., Sephadex G25 fast-desalting spin columns or Pharmacia HR 10/10 columns, in an off-line format of the method) are handled according to the manufacturer's instructions. For instance, G25 columns are first washed with 100 μL water and centrifuged at 3000 rpm (~900 g) at 4° C. for 5 min. The reaction mixtures are then loaded on the columns and centrifuged as before. Unbound compounds should be retained on the columns, while any protein, bound or unbound to low molecular weight candidate compounds, should flow through the column. Protein complexes in the flow-through of spin columns are collected. The protein-ligand complex in the eluted fraction is then denatured by adding 100 μL ACN solution containing 0.1% trifluoroacetic acid (TFA) (Sigma Chemical CO.), incubating for 5 min at room temperature, and vortexing for 15 seconds. The denatured protein is removed by centrifugation at 10 000 g for about 30 seconds.

Exemplary Ultrafiltration Protocol

The supernatant liquid resulting from the gel filtration protocol is then subjected to a denaturation procedure and applied to the second size-exclusion separation medium, preferably an ultrafiltration membrane. Examples are ultrafiltration membranes having a 20,000, 10,000, or 3,000 Dalton cut-off sold as Microcon-3, by Amicon, Beverly, Mass., USA. Preferred are membranes with a cut-off of about 10,000 Da (which lets pass about 1% of molecules over 30,000 Da), or less. A membrane with a 3,000 Da cut-off lets pass only about 0.1% of materials over 30,000 Da. Most preferred are ultrafiltration membranes that can withstand 100% organic solvents (e.g., ACN) and organic acids (e.g., TFA or acetic acid).

Ultrafiltration membranes having other small molecular weight cut-offs, e.g., within the range of about 1000–5000 Da, preferably 2000–4000 Da, are also available commercially (e.g., All Filtron Co., Northborough, Mass., 5000 Da cut-off).

Exemplary MS or LC-MS Protocol

The ultrafiltered liquid (containing any candidate ligand that bound to the target), is then analyzed by mass spectrometry alone or by liquid chromatography coupled to mass spectrometry, or other analytical techniques such as IR spectroscopy or NMR, for the presence of released small molecular weight compounds, after lyophilization and re-suspension in small volumes.

Mass spectrometry: Analysis can be performed on, e.g., ion trap triple quadrupole mass spectrometers LCQ (Thermo-Quert Corporation, San Jose, Calif., USA) or APCI. The electrospray voltage is generally maintained in the range of about +4.5–4.75 kV. Ion optics settings are optimized on the day of the analysis to provide the maximum efficiency of ion to the detector. The effective mass range is generally from m/z 150 to m/z 700 at a rate of about 1 s/scan.

Liquid chromatography: For example, samples can be introduced through a HP1100 (Hewlett Packard Paulo Alto, Calif. USA) chromatography operating in the gradient mode at a flow rate of 1 ml/min. An Inertsil C18 base-deactivated microbore column (4.6 mm×10 cm) from MetaChem Technologies (Torrance, Calif., USA) is used for sample separation. The mobile phase gradient is Milli-Q $H_2O$+ACN 90/10 (v/v) to a $H_2O$+ACN 0/100 (v/v) in 15 minutes. Samples are introduced through a Rheodyne Model 7125 injector (Cotati, Calif., USA) with a 10 μL external loop. The sample injection volumes are generally 1–19 μL.

EXAMPLE I (Off-line Format)

The off-line screening procedure of the invention is demonstrated using human carbonic anhydrase II (CAII) as a target, and a natural sample (NS) inactive toward CAII (e.g., inert fungal extract) that is spiked with a known, small molecule ligand that binds specifically to the active site of CAII, acetazolamide (AZ). Approximately 20 μM (micromolar) of CAII was mixed and incubated with approximately 1 microgram of an inactive natural sample containing about 10 μM (micromolar) of AZ in a buffered solution such as phosphate buffered saline, pH 7.0, 1% DMSO, for final CAII and AZ concentrations of about 1 micromolar. Size-exclusion chromatography was performed using a Pharmacia HR 10/10 column at 4 ml/min using a mobile phase of 200 mM ammonium acetate, pH 7.0. Typically, the excluded volume containing the target protein (CAII) with bound ligand (AZ), elutes from the column in about 0.6–0.7 minutes under such conditions.

Figure 3A:
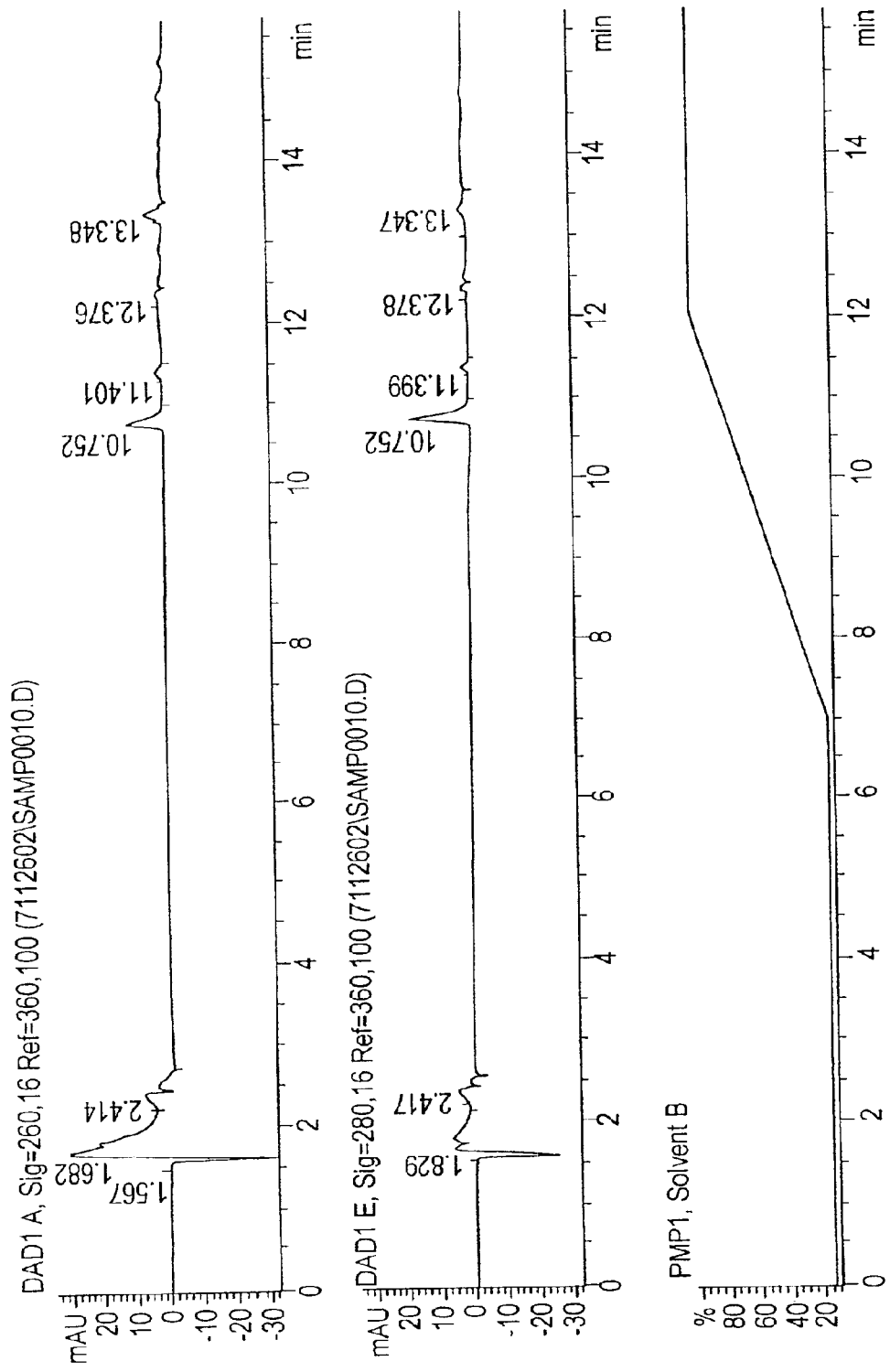
FIGS. 3A–C show liquid chromatography-mass spectrometry (LC-MS) chromatograms from using an off-line embodiment of the method to screen for a ligand, acetazolamide, which binds to human carbonic anhydrase II.
Figure 3B:
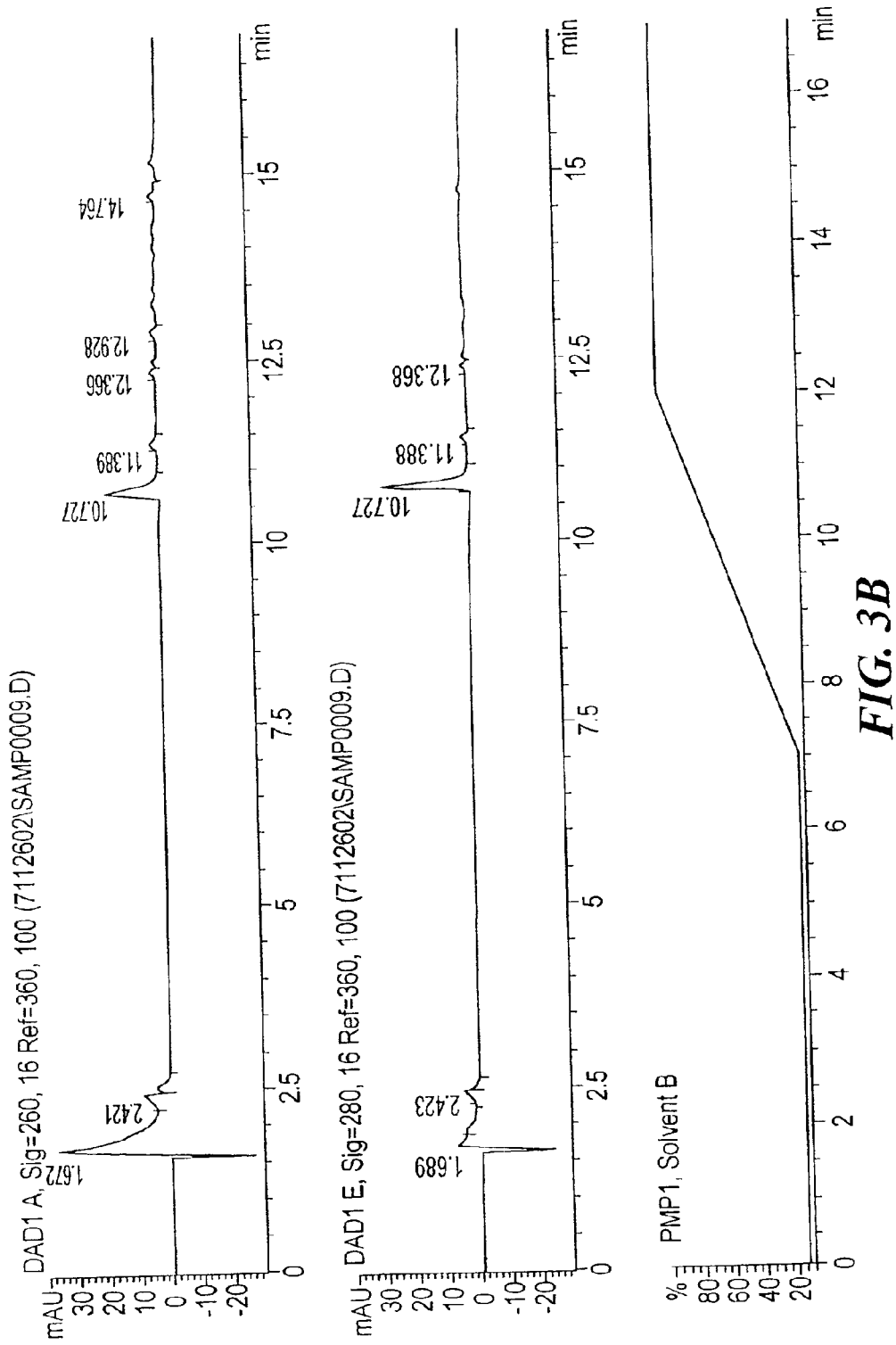
Figure 3C:
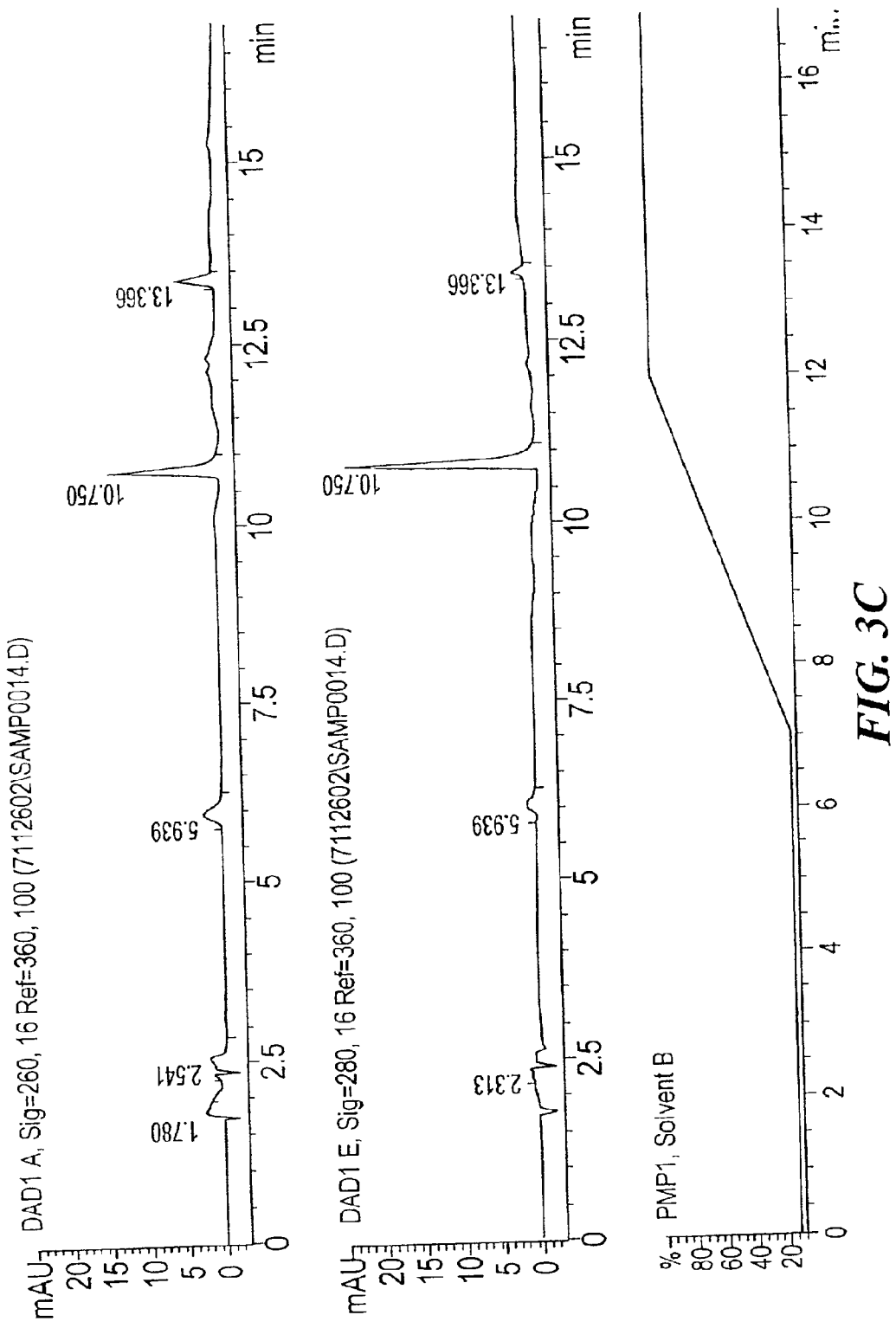

FIG. 3A shows an LC-MS chromatogram of a blank experiment, where about 20 μM (micromolar) CAII alone was passed through the entire method of the invention. FIG. 3B depicts the LC-MS chromatogram from performing the same with that amount of CAII incubated with the inactive natural sample (NS) alone. There are no additional peaks detected, compared to the blank experiment, which indicates the absence of target-binding ligands from the inactive biological sample. FIG. 3C shows the LC-MS results from performing the same screening process with a natural (NS) sample now containing about 10 μM (micromolar) of the CAII-binding ligand, acetazolamide (AZ). Active ligand was successfully extracted from the inactive complex biological matrix as a result of the screening method of the invention. As shown in FIGS. 3A–3C, target CAII (TG) peaks are a series of chromatographic peaks having retention times of 10.5 min. and longer. The ligand AZ peak has a retention time of 5.9 min.

Those skilled in the art will recognize, or be able to ascertain using no more than routine experimentation, many equivalents of the specific embodiments of the invention described herein. Such equivalents are intended to be encompassed by the following claims.

What is claimed is:

1. A method of screening a sample of complex biological material for an affinity ligand that binds to a protein target, comprising:
   (1) mixing a protein target and a sample of complex biological material in solution to form a reaction mixture;
   (2) incubating the reaction mixture wider conditions allowing complex formation by the target and any target-binding ligand present in the sample;
   (3) passing the reaction mixture through a first size-exclusion medium that removes from the reaction mixture any small molecular weight compounds each having a molecular weight less than a first preset value;
   (4) subjecting the size-excluded reaction mixture from step (3) to conditions promoting dissociation of any ligand/target complex into free ligand and free target; and
   (5) passing the reaction mixture resulting from step (4) through a second size exclusion medium that removes from the reaction mixture any molecule larger than a second preset value.

2. The method of claim 1, wherein the first size-exclusion medium removes molecules having a molecular weight of about 2,000 daltons or less.

3. The method of claim 1, wherein the first size-exclusion medium removes molecules having a molecular weight of about 1,500 daltons or less.

4. The method of claim 1, wherein the first size-exclusion medium comprises a gel filtration or size exclusion HPLC column.

5. The method of claim 1, wherein step (4) comprises adding to the size-excluded mixture from step (3), a solution comprising an organic solvent and an organic acid.

6. The method according to claims 1, 4, or 5, wherein the second size-exclusion medium comprises an ultrafiltration membrane.

7. The method according to claims 1, 4, or 5, wherein the second size-exclusion medium removes from the reaction mixture, molecules having a molecular weight of about 10,000 daltons or more.

8. The method according to claims 1, 4, or 5, wherein the second size-exclusion medium removes from the reaction mixture, molecules having a molecular weight of about 3,000 daltons or more.

9. The method according to claims 1, 4, or 5, wherein the second size-exclusion medium removes from the reaction mixture, molecules having a molecular weight of about 2,000 daltons or more.

10. The method of claim 6, wherein the ultrafiltration membrane removes from the reaction mixture, molecules having a molecular weight of about 10,000 daltons or more.

11. The method of claim 6, wherein the ultrafiltration membrane removes from the reaction mixture, molecules having a molecular weight of about 3,000 daltons or more.

12. The method of claim 6, wherein the ultrafiltration membrane removes from the reaction mixture, molecules having a molecular weight of about 2,000 daltons or more.

13. The method according to claims 1, 4, or 5, further comprising, after step (5):
   (6) subjecting the reaction mixture resulting from step (5), to at least one structural or functional analysis.

14. The method according to claim 13, further comprising:
   (7) comparing the analytical results of step (6) with a reference standard.

15. The method of claim 14, wherein the reference standard comprises the analytical results of subjecting either a sample of the protein target alone or a mixture of the protein target with a non-target-binding natural sample, to steps (2)–(6).

16. The method of claim 13, wherein the at least one analysis in step (6) comprises a member selected from the group consisting of mass spectrometry analysis; liquid chromatography; liquid chromatography coupled on-line with mass spectrometry analysis; infrared spectroscopy; nuclear magnetic resonance; an alternative binding assay; a biochemical assay; a cell-based reporter assay; and an ELISA-based assay.

17. The method according to claim 1, 4, or 5, further comprising, in step (1), including a known competitive ligand that binds to the target in the reaction mixture prior to step (2).

18. The method of claim 17, wherein the concentrations of the known competitive ligand and the target are approximately equimolar.

19. The method of claim 17, wherein the known competitive ligand concentration is within a range of approximately twice to 10 times the target concentration.

20. The method of claim 17, wherein the known competitive ligand concentration is approximately 5 times the target concentration.

21. The method of claim 17, further comprising the step (7) of comparing the analytical results of step (6) with a reference standard.

22. The method of claim 21, wherein the reference standard comprises the analytical results of subjecting a mixture of the protein target and the known competive ligand, in the absence of any other target-binding ligand, to steps (2)–(6).

* * * * *